(12) United States Patent
Zhao et al.

(10) Patent No.: US 11,357,804 B2
(45) Date of Patent: Jun. 14, 2022

(54) APPLICATION OF ONCOLYTIC VIRUSES AS IMMUNOSTIMULANTS FOR TREATMENT OF TUMORS AND/OR CANCERS

(71) Applicant: HANGZHOU CONVERD CO., LTD., Hangzhou (CN)

(72) Inventors: Ronghua Zhao, Hangzhou (CN); Yanjun Zheng, Hangzhou (CN); Fang Hu, Hangzhou (CN)

(73) Assignee: HANGZHOU CONVERD CO., LTD., Hangzhou (CN)

( * ) Notice: Subject to any disclaimer, the term of this patent is extended or adjusted under 35 U.S.C. 154(b) by 315 days.

(21) Appl. No.: 16/478,727

(22) PCT Filed: Jan. 24, 2018

(86) PCT No.: PCT/CN2018/073954
§ 371 (c)(1),
(2) Date: Jul. 17, 2019

(87) PCT Pub. No.: WO2018/137643
PCT Pub. Date: Aug. 2, 2018

(65) Prior Publication Data
US 2020/0138882 A1    May 7, 2020

(30) Foreign Application Priority Data
Jan. 25, 2017   (CN) .......................... 201710056371.5

(51) Int. Cl.
*A61K 35/761* (2015.01)
*A61P 37/02* (2006.01)
*A61P 35/00* (2006.01)
*C12N 7/00* (2006.01)

(52) U.S. Cl.
CPC ............ *A61K 35/761* (2013.01); *A61P 35/00* (2018.01); *A61P 37/02* (2018.01); *C12N 7/00* (2013.01)

(58) Field of Classification Search
CPC .................................................... A61K 35/761
See application file for complete search history.

(56) References Cited

U.S. PATENT DOCUMENTS

| 5,677,178 A | 10/1997 | McCormick |
| 2014/0377221 A1 | 12/2014 | Tufaro et al. |
| 2016/0289645 A1 | 10/2016 | Tufaro et al. |

FOREIGN PATENT DOCUMENTS

| CN | 1110553 C | 6/2003 |
| CN | 101304761 | 11/2008 |

OTHER PUBLICATIONS

Lu et al. (World J Gastroenterol 2004;10(24):3634-3638) (Year: 2004).*
Connolly et al. (Thromb Res. Aug. 2010; 126(2): 113-118.). (Year: 2010).*
Huang et al. (Drug Discovery Today vol. 14, Issues 11-12, Jun. 2009, pp. 570-578). (Year: 2009).*
Lei et al. (International Journal of Oncology 47: 555-562, 2015) (Year: 2015).*
Heise et al. (Nature Medicine. vol. 3, No. 6 pp. 639-645; Jun. 1997) (Year: 1997).*
Jian'gang et al., "Oncolytic Viruses for Cancer Treatment", Journal of Microbes and Infections) Mar. 31, 2009.
International Search Report dated Apr. 11, 2018.
Danyang et al., "The Progress of Oncolytic Vaccinia Viruses Modified Genetically for the Tumor Treatment" Jul. 11, 2016.
CN Office Action dated Dec. 28, 2020.
Office Action dated Jul. 7, 2021.

* cited by examiner

*Primary Examiner* — Scott Long
(74) *Attorney, Agent, or Firm* — Ipsilon USA, LLP

(57) ABSTRACT

Provided is the use of selectively replicating oncolytic viruses in the preparation of immunostimulants for treatment of tumors and/or cancers, wherein the oncolytic viruses do not carry exogenous immunoregulatory genes.

5 Claims, 16 Drawing Sheets

Day 13 after PBS injection    Day 13 after H101 injection

APPLICATION OF ONCOLYTIC VIRUSES AS IMMUNOSTIMULANTS FOR TREATMENT OF TUMORS AND/OR CANCERS

FIELD OF THE INVENTION

The present invention relates to the field of biomedicine, and particularly to uses of oncolytic viruses as immunostimulants for treatment of tumors and/or cancers.

BACKGROUND OF THE INVENTION

Biological therapy for tumors is the fourth modality of tumor/cancer treatment developed after surgery, radiotherapy and chemotherapy. Tumor immunotherapy is one of the most effective methods in the biological therapy for tumors. Due to the heterogeneity in tumors, the mutation of tumor cells and the immune escape phenomenon caused by the microenvironment of tumor tissues, it is not quite effective to stimulate immunity of the body and induce specific T cells to kill tumors by relying solely on a single kind of tumor-specific antigen (see Fridman et al., 2012, The immune contexture in human tumours: impact on clinical outcome, Nature reviews Cancer, 12, 298-306). These obstacles are highlighted in the immunocyte therapy for solid tumors. Currently, single-target immunocyte therapy still only works well on CD19-targeted hematological tumors (see Khalil et al., 2016, The future of cancer treatment: immunomodulation, CARs and combination immunotherapy, Nature reviews Clinical oncology, 13, 273-290). At present, the worldwide problem faced by academics and research communities is how to effectively stimulate the anti-tumor immunity of the body and avoid the tumor immune escape.

Tumor immunotherapy takes effect mainly by the tumor-specific T cell immune response in vivo (see Palucka and Banchereau, 2012, Cancer immunotherapy via dendritic cells, Nature reviews Cancer, 12, 265-277). Among others, the core anti-tumor immune cycle includes seven steps as described below.

In the first step, tumor tissues are induced by the combined action of internal and external factors to release neoantigens that can induce specific cellular immunity (step 1). The release of these tumor-specific neoantigens should be accompanied by generation of other immune-stimulating signals in the body at the same time, so as to avoid the occurrence of immune tolerance. Such signals may include proinflammatory cytokines, and factors released by dead cells or by the gut microbiota. Next, dentritic cells (DCs) capture the neoantigen epitope signals by MHC Class I (also referred to as MHCI or MHC-I) and MHC Class II (also referred to as MHCII or MHC-II) molecules on the surface thereof, such that the DCs are activated and transmit the specific activation signals to T cells (step 2). The T cell clones that have received the specific DC antigen signals are activated and amplified (step 3). Here, such neoantigens are taken by the immune system as exogenous antigens, or as endogenous antigens that do not go through an immune tolerance process during the developmental stage yet. However, the final outcome of the immune activation will be manifested by the immune system status at this time. For example, the ratio of effector T cells to regulatory T cells (Treg) can largely determine the immune effect. Immune cells such as these activated tumor-specific T cells are attracted by chemokines that are induced by inflammation or immunostimulants, thereby homing to the vicinity of the tumor sites (step 4). Then, specific cytotoxic T lymphocytes (CTLs)/helper T cells break through various barriers and infiltrate the tumor entities (step 5). The CTLs specifically recognize and bind to MHCI-matched cancer cells through the T cell receptor (TCR) and tumor-specific antigens (step 6). Finally, the CTLs kill their target cells (step 7). Again, the killed tumor cells release tumor-associated antigens (TAAs) (step 1) to further broaden the spectrum of antigens and enhance the anti-tumor immunity (see Chen and Mellman, 2013, Oncology meets immunology: the cancer-immunity cycle, Immunity, 39, 1-10).

However, in clinical practice, the above anti-tumor immune cycle in many cancer patients is not optimized by treatment. For example, the tumor neoantigens are not effectively released; DCs and T cells cannot effectively recognize tumor antigens; too many Treg cell responses are induced to generate immune tolerance; activated T cells cannot effectively home to tumor lesions; and more importantly, tumor lesions are maintained in an immunosuppressive microenvironment for a long time, preventing the infiltrating effector T cells from effectively killing tumors (see Motz and Coukos, 2013, Deciphering and reversing tumor immune suppression, Immunity, 39, 61-73). Therefore, one of the core tasks of tumor immunotherapy is to find effective immunostimulants to activate the immune system and inhibit the occurrence of negative effects.

Immunostimulants used in tumor immunotherapy are a class of stimulatory modulators for tumor immunotherapy that can stimulate the immune system to destroy tumors, and they include various recombinant, synthetic, and natural agents. There are a variety of strategic approaches in specific practice, research, and experiments. Some reports of randomized controlled clinical studies have shown that in the immunotherapies for different types of cancers, the patient's survival time and disease-free period are both significantly improved, and when combined with a conventional treatment, the efficacy increases by 20% to 30% (see Fridman et al., 2012, The immune contexture in human tumours: impact on clinical outcome, Nature reviews Cancer, 12, 298-306; Khalil et al., 2016, The future of cancer treatment: immunomodulation, CARs and combination immunotherapy, Nature reviews Clinical oncology, 13, 273-290; Kono et al., 2002, Prognostic significance of adoptive immunotherapy with tumor-associated lymphocytes in patients with advanced gastric cancer: a randomized trial, Clinical cancer research: an official journal of the American Association for Cancer Research, 8, 1767-1771; and Takayama et al., 2000, Adoptive immunotherapy to lower postsurgical recurrence rates of hepatocellular carcinoma: a randomised trial, Lancet, 356, 802-807). Immunostimulants commonly known in the art include: some interleukin cytokines having immunostimulatory effect, such as IL-1, IL-2, IL-7, IL-12, IL-15 and IL-21 (see Floros and Tarhini, 2015, Anticancer Cytokines: Biology and Clinical Effects of Interferon-alpha2, Interleukin (IL)-2, IL-15, IL-21, and IL-12, Seminars in oncology, 42, 539-548; Gao et al., 2015, Mechanism of Action of IL-7 and Its Potential Applications and Limitations in Cancer Immunotherapy, International journal of molecular sciences, 16, 10267-10280; Whittington and Faulds, 1993, Interleukin-2. A review of its pharmacological properties and therapeutic use in patients with cancer, Drugs, 46, 446-514); interferons, such as IFN-alpha (see Galani et al., 2016, IFNs-signaling effects on lung cancer: an up-to-date pathways-specific review, Clinical and experimental medicine); colony stimulating factors, such as G-CSF and GM-CSF (see Hoeller et al., 2016, Systematic review of the use of granulocyte-macrophage colony-stimulating factor in patients with advanced melanoma, Cancer immunology, immunotherapy: CII, 65, 1015-1034; and Li et al., 2005, Preclinical ex vivo expansion of G-CSF-mobilized peripheral blood stem cells: effects of serum-free media, cytokine combinations and chemotherapy, European journal of haematology, 74, 128-135); tumor necrosis factors, such as TNF-alpha; immune cytokines, such as CD40L/CD40 (see Lippitz, 2013, Cytokine patterns in patients with cancer: a systematic review, The Lancet Oncology, 14, e218-228); chemotactic factors, such as CCL-3, CCL-5, CCL-26, CX3CL1, CXCL9 and CXCL10 (see Elbaz et al., 2015, Modulation of the tumor microenvironment and inhibition of EGF/EGFR pathway: novel anti-tumor mechanisms of Cannabidiol in breast cancer, Molecular oncology, 9, 906-919; Franciszkiewicz et al., 2012, Role of chemokines and chemokine receptors in shaping the effector phase of the antitumor immune response, Cancer research, 72, 6325-6332; Fridman et al., 2012, The immune contexture in human tumours: impact on clinical outcome, Nature reviews Cancer, 12, 298-306; Khalid et al., 2015, Recent Advances in Discovering the Role of CCL5 in Metastatic Breast Cancer, Mini reviews in medicinal chemistry, 15, 1063-1072; Mellman et al., 2011, Cancer immunotherapy comes of age, Nature, 480, 480-489; Peng et al., 2012, PD-1 blockade enhances T-cell migration to tumors by elevating IFN-gamma inducible chemokines, Cancer research, 72, 5209-5218; and Tudoran et al., 2015, Baseline blood immunological profiling differentiates between Her2-breast cancer molecular subtypes: implications for immunomediated mechanisms of treatment response, OncoTargets and therapy, 8, 3415-3423); Toll-like receptor (TLR) signal-related molecules (see Mellman et al., 2011, Cancer immunotherapy comes of age, Nature, 480, 480-489); and immune checkpoint related agents, such as anti-PD-1 antibodies and anti-CTLA4 antibodies.

Oncolytic viruses can selectively replicate in tumor cells and kill them. Compared with traditional chemotherapy and radiotherapy, oncolytic viruses have almost no toxicity to normal human cells. Compared with targeted drugs, oncolytic viruses can self-replicate in tumors, continuously infect and lyse tumor cells, and produce long-lasting efficacy. Moreover, oncolytic viruses can be used as gene therapy vectors to efficiently express various anti-tumor genes in vivo, including toxic genes related to specific killing of tumor cells, cytokine genes for stimulating immunity and the like. For example, the internationally marketed Talimogene laherparepvec (T-Vec, trade name: Imlygic, also known as OncoVex GM-CSF) is a tumor immunotherapy agent prepared by inserting human GM-CSF (granulocyte-macrophage colony-stimulating factor) gene into a genetically modified HSV-I (herpes simplex virus type 1), so as to induce anti-tumor immunity by the oncolytic effect of HSV-I oncolytic virus combined with the immunostimulatory effect of GM-CSF (see Sheridan, 2013, Amgen announces oncolytic virus shrinks tumors, Nature biotechnology, 31, 471-472). Since the agent comprises the inserted foreign gene, it is impossible to identify the immunostimulatory effect of the HSV-1 oncolytic virus per se, and the pharmacological action of the agent is mostly manifested by the inserted GM-CSF gene. However, the GM-CSF, as an immunoregulatory cytokine, behaves like a double-edged sword and has been shown to inhibit tumor immunity in some research models (see De Henau et al., 2016, Overcoming resistance to checkpoint blockade therapy by targeting PI3Kgamma in myeloid cells, Nature, 539, 443-447). In the immunotherapy for tumors and/or cancers, there is still a need for effective immunostimulants to activate the immune system.

SUMMARY OF THE INVENTION

In order to solve the above-mentioned problems in the art, the present disclosure provides the use of a selectively replicating oncolytic virus in the preparation of an immunostimulant for treatment of tumors and/or cancers, and a method for treating a tumor and/or cancer using the oncolytic virus as an immunostimulant.

In particular, the present disclosure provides:

(1) Use of a selectively replicating oncolytic virus in the preparation of an immunostimulant for treatment of tumors and/or cancers, wherein the oncolytic virus does not carry an exogenous immunoregulatory gene, and wherein a subject to whom the immunostimulant is to be administered is a tumor and/or cancer patient whose immune function is sufficient to cause an anti-tumor cellular immune response, wherein the total number of leukocytes in whole blood of the tumor and/or cancer patient is $\geq 4.0 \times 10^9$/L.

(2) The use according to item (1), wherein, in addition to directly killing tumor and/or cancer cells, the oncolytic virus can also effectively induce activation and amplification of dendritic cells and T cells, induce up-regulation of the expression of chemokines at tumor and/or cancer cell sites, promote the infiltration of dendritic cells and lymphocytes at tumor and/or cancer cell sites, and induce up-regulation of the expression of MHC-I and/or MHC-II molecules on tumor and/or cancer cells, thereby comprehensively stimulating the anti-tumor immune response of the patient.

(3) The use according to item (1), wherein the oncolytic virus is a human adenovirus type 5, a human 5/3 chimeric adenovirus or a human 5/2 chimeric adenovirus; preferably, the virus cannot express E1B-55KD polypeptide or the E1A protein of the virus is deleted partially; and more preferably, the oncolytic virus is H101.

(4) The use according to item (1), wherein the immunostimulant is administered in combination with one or more other tumor immunological agents.

(5) The use according to item (1), wherein the immunostimulant comprises the oncolytic virus at a dose ranging from $0.5 \times 10^{12}$ to $1.5 \times 10^{12}$ vp/day.

(6) A method for treating a tumor and/or cancer, including administering to a tumor and/or cancer patient an immunostimulating effective amount of a selectively replicating oncolytic virus as an immunostimulant in the treatment of the tumor and/or cancer, wherein the oncolytic virus does not carry an exogenous immunoregulatory gene, and wherein the immune function of the patient is sufficient to cause an anti-tumor cellular immune response, and the total number of leukocytes in whole blood of the patient is $\geq 4.0 \times 10^9$/L.

(7) The method according to item (6), wherein, in addition to directly killing tumor and/or cancer cells, the oncolytic virus can also effectively induce activation and amplification of dendritic cells and T cells, induce up-regulation of the expression of chemokines at tumor and/or cancer cell sites, promote the infiltration of dendritic cells and lymphocytes at tumor and/or cancer cell sites, and induce up-regulation of the expression of MHC-I and/or MHC-II molecules on tumor and/or cancer cells, thereby comprehensively stimulating the anti-tumor immune response of the patient.

(8) The method according to item (6), wherein the oncolytic virus is a human adenovirus type 5, a human 5/3 chimeric adenovirus or a human 5/2 chimeric adenovirus; preferably, the virus cannot express E1B-55KD polypeptide or the E1A protein of the virus is deleted partially; and more preferably, the oncolytic virus is H101.

(9) The method according to item (6), wherein the immunostimulant is administered via intratumoral injection at a dose of $0.5\times10^{12}$ to $1.5\times10^{12}$ vp/day of the oncolytic virus, once daily, consecutively for 4 to 5 days.

(10) The method according to item (6), wherein the immunostimulant is administered in combination with one or more other tumor immunological agents.

(11) The method according to item (9), wherein, 7-10 days after completion of the first course of consecutive administration, the immunostimulant is administered again to carry out an immune-boosting course, wherein the immune-boosting course is performed via intratumoral injection at a dose of $0.5\times10^{12}$ to $1.5\times10^{12}$ vp/day of the oncolytic virus, once daily, consecutively for 1 to 2 days.

(12) The method according to item (11), wherein the immune-boosting course is further repeated 2 to 3 times, at an interval of 7-10 days from the end of one immune-boosting course to the beginning of the next immune-boosting course.

The present disclosure has the following advantages and positive effects compared to the prior art:

Based on long-term research and experiments, the present inventors have discovered a novel use of oncolytic viruses. Specifically, the inventors have found that the oncolytic viruses, without the need to undergo more genetic modification to carry an exogenous immunoregulatory gene, can be used as immunostimulants in the treatment of tumors and/or cancers to individualizedly induce the release of tumor antigens in vivo and act on all the seven steps of the anti-tumor immune system of the body, thereby comprehensively activating the anti-tumor immune function, achieving secondary attack on tumors, and producing sustained efficacy.

In contrast to the existing anti-tumor mechanisms of oncolytic viruses (e.g., H101) and therapeutic concepts, the present disclosure develops a new principle and a new usage of oncolytic viruses against tumors, in which the oncolytic viruses are administered as effective immunostimulants.

The inventors have found that the oncolytic viruses according to the present disclosure can participate in all the seven steps of anti-tumor immunization and produce the following immunopromoting effects in the respective steps, even if they are administered alone without any other immunotherapy being used in combination:

1) lyse tumors and promote the release of tumor antigens;
2) upregulate the DC content in peripheral blood and promote the activation of APCs (antigen-presenting cells);
3) upregulate the T cell content in peripheral blood;
4) stimulate the release of chemokines at tumor sites and facilitate the homing and aggregation of immune cells at tumor sites;
5) promote infiltration of DCs and $CD8^+$ CTLs into tumor entities;
6) stimulate the expression of MHCI/II on tumor cells and promote immune recognition; and
7) effectively reduce the tumor burden and induce further release of tumor antigens by the combination of oncolysis and immune killing effects of the oncolytic viruses.

The inventors have found that the oncolytic viruses according to the present disclosure can be administered alone as immunostimulants in the treatment of tumors and/or cancers, in which the oncolytic effect of the oncolytic viruses can function together with the immunostimulatory effect thereof, resulting in improved efficacy.

BRIEF DESCRIPTION OF THE DRAWINGS

FIG. 1 shows the results of MTT assay of in vitro infection of human and murine tumor cell lines with H101 in Experimental example 1 according to the present disclosure, wherein

FIG. 2 shows the results of H101 promoting apoptosis and tumor antigen release in Experimental example 2 according to the present disclosure, wherein

FIG. 3 shows the results of H101 activating dendritic cells in Experimental example 3 according to the present disclosure, wherein

FIG. 4 shows the results of H101 activating T cells in Experimental example 4 according to the present disclosure, wherein

FIG. 6 shows the results of H101 promoting infiltration of NKs, DCs and CTLs into tumor entities in Experimental example 6 according to the present disclosure, wherein

FIG. 7 shows the results of H101 stimulating the MHCI/II expression of tumor cells in Experimental example 7 according to the present disclosure, wherein

FIG. 8 shows the results of relative inhibition of tumor growth by H101 in Experimental example 8 according to the present disclosure, wherein

DETAILED DESCRIPTION OF THE INVENTION

Figure 1A:
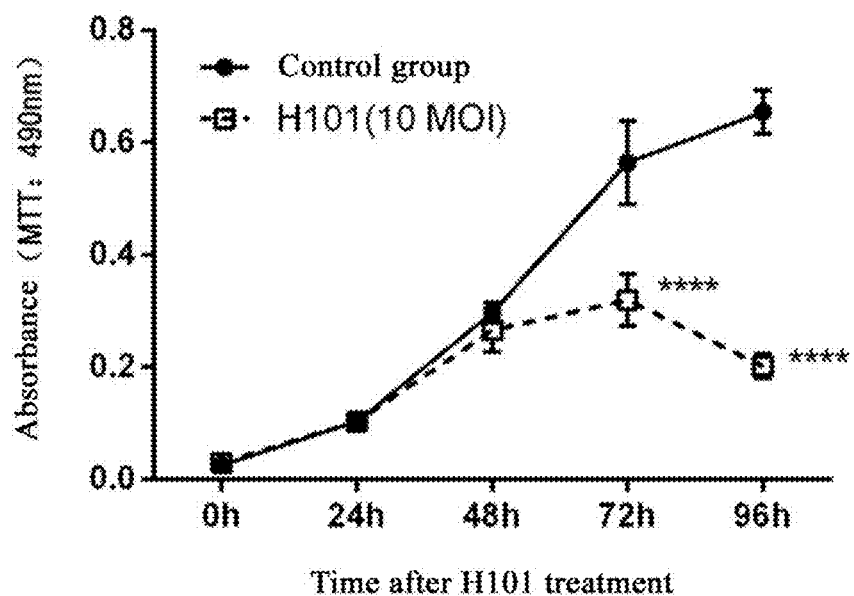
FIG. 1A shows the results of A549 cells infected with H101.

The present disclosure is further explained by the following description of the embodiments and with reference to the accompanied drawings, but it is not intended to limit the invention, and those skilled in the art can make various modifications or improvements according to the spirit of the disclosure. The modifications and improvements are within the scope of the disclosure, without departing from the spirit of the disclosure.

Current treatments of tumors and/or cancers by oncolytic viruses primarily utilize the mechanism that oncolytic viruses can specifically replicate in tumor cells and cause lysis and death of the cells. U.S. Pat. No. 5,677,178 discloses an oncolytic adenovirus, ONYX-015, which is a specific oncolytic adenovirus constructed by deleting E1B-55KD fragment in the DNA sequence of human wild-type adenovirus type 5. ONYX-015 has no significant effect on normal cells, but can selectively replicate and proliferate in tumor cells, eventually leading to lysis of the tumor cells. The clinical trials of ONYX-015 for the treatment of malignant tumors were started in 1996 in subjects with tumors such as head and neck tumor, brain glioma, pancreatic cancer, primary liver and gallbladder tumor, hepatic metastases from colorectal cancer, non-small cell lung cancer, cervical cancer and the like, and the results indicated that the treatment is effective and safe to a certain extent. Also, Chinese Patent No. CN1110553C discloses an oncolytic adenovirus, H101 (CCTCC Deposit No.: V98003), which is an oncolytic adenovirus obtained by genetic recombination of human adenovirus type 5 (Ad5) using genetic engineering techniques. H101 cannot express E1B-55KD polypeptide and lacks the E3 region. Since H101 can specifically replicate in tumor cells, eventually leading to lysis of the cells, oncolytic efficacy can be achieved. H101 was approved by CFDA for sale in China in 2006, with the New Drug Application (NDA) No. Guo Yao Zhun Zi S20060027, under the trade name "Oncorine".

The therapeutic concept and the purpose of application of the above-mentioned oncolytic viral agents are identical to many other specific targeting anti-tumor drugs that have been developed so far, and they are all used as drugs which are expected to directly act on tumors per se and thereby inhibit the same. In other words, these agents take advantage of the function that oncolytic viruses can selectively replicate in tumor cells to cause lysis and death of the cells.

However, based on long-term research and experiments, the present inventors have discovered a novel use of oncolytic viruses. Specifically, the inventors have found that the oncolytic viruses according to the present disclosure can be used as immunostimulants in the treatment of tumors and/or cancers to individualizedly induce the release of tumor antigens in vivo and act on all the seven steps of the anti-tumor immune system, thereby comprehensively activating the anti-tumor immune function, achieving secondary attack on tumors, and producing sustained efficacy.

The inventors have found that the oncolytic viruses according to the present disclosure can function to stimulate all the steps of anti-tumor immune responses and comprehensively activate the anti-tumor immune function of the body, without the need to undergo more genetic modification to carry an exogenous immunoregulatory gene. Therefore, unlike T-Vec, the inventors have found that the selectively replicating oncolytic viruses per se (without carrying an exogenous immunoregulatory gene) can be used as immunostimulants in the treatment of tumors and/or cancers.

In addition, in order to better exert the function of the immunostimulants, the inventors have further found that the subject to whom the immunostimulant is to be administered should be a tumor and/or cancer patient whose immune function is sufficient to cause an anti-tumor cellular immune response, and the total number of leukocytes in whole blood of the tumor and/or cancer patient should be greater than or equal to $4.0 \times 10^9$/L.

Based on the above findings, the present disclosure provides the use of a selectively replicating oncolytic virus in the preparation of an immunostimulant for treatment of tumors and/or cancers, wherein the oncolytic virus does not carry an exogenous immunoregulatory gene, and wherein a subject to whom the immunostimulant is to be administered is a tumor and/or cancer patient whose immune function is sufficient to cause an anti-tumor cellular immune response, wherein the total number of leukocytes in whole blood of the tumor and/or cancer patient is $4.0 \times 10^9$/L.

In addition to directly killing tumor and/or cancer cells, the oncolytic virus can also effectively induce activation and amplification of dendritic cells and T cells, induce up-regulation of the expression of chemokines at tumor and/or cancer cell sites, promote the infiltration of dendritic cells and lymphocytes at tumor and/or cancer cell sites, and induce up-regulation of the expression of MHC-I and/or MHC-II molecules on tumor and/or cancer cells, thereby comprehensively stimulating the anti-tumor immune response of the patient.

According to the present disclosure, the oncolytic virus is preferably a human adenovirus type 5, a human 5/3 chimeric adenovirus or a human 5/2 chimeric adenovirus. Preferably, the virus cannot express E1B-55KD polypeptide or the E1A protein of the virus is deleted partially. More preferably, the oncolytic virus lacks at least a portion of genes in the E3 region. Still more preferably, the oncolytic virus is H101.

Preferably, the immunostimulant comprises the oncolytic virus at a clinically applied dosage, e.g., $0.5\times10^{12}$ to $1.5\times10^{12}$ vp/day.

The oncolytic virus as the immunostimulant may be administered via intratumoral or intravenous injection at a dose of $0.5\times10^{12}$ to $1.5\times10^{12}$ vp/day of the oncolytic virus, once daily, consecutively for 4 to 5 days. Alternatively, the oncolytic virus may be loaded into a cell carrier and administered by infusion. For example, the oncolytic virus may be loaded into autologous or allogeneic immune cells that are cultured in vitro, and then administered by intravenous infusion or the like (see Ilett et al., 2009, Dendritic cells and T cells deliver oncolytic reovirus for tumour killing despite pre-existing anti-viral immunity, Gene therapy, 16, 689-699).

Also, the immunostimulant according to the present disclosure may be administered in combination with one or more other tumor immunological agents including, but not limited to, some interleukin cytokines having immunostimulatory effect, such as IL-1, IL-2, IL-7, IL-12, IL-15, and IL-21; interferons, such as IFN-alpha; colony-stimulating factors, such as G-CSF, and GM-CSF; tumor necrosis factors, such as TNF-alpha; immune cytokines, such as CD40L/CD40; chemokines, such as CCL-3, CCL-5, CCL-26, CX3CL1, CXCL9, and CXCL10; Toll-like receptor (TLR) signal-related molecules; and immune checkpoint related agents, such as anti-PD-1 antibodies and anti-CTLA4 antibodies.

In another aspect, the present disclosure provides a method for treating a tumor and/or cancer, including administering to a tumor and/or cancer patient an immunostimulating effective amount of the selectively replicating oncolytic virus according to the present disclosure as an immunostimulant in the treatment of the tumor and/or cancer, wherein the oncolytic virus does not carry an exogenous immunoregulatory gene, and wherein the immune function of the patient is sufficient to cause an anti-tumor cellular immune response, and the total number of leukocytes in whole blood of the patient is $\geq 4.0\times10^9$/L.

In the method according to the present disclosure, in addition to directly killing tumor and/or cancer cells, the oncolytic virus can also effectively induce activation and amplification of dendritic cells and T cells, induce up-regulation of the expression of chemokines at tumor and/or cancer cell sites, promote the infiltration of the dendritic cells and lymphocytes at tumor and/or cancer cell sites, and induce up-regulation of the expression of MHC-I and/or MHC-II molecules on tumor and/or cancer cells, thereby comprehensively stimulating the anti-tumor immune response of the patient.

In the method, the immunostimulant is preferably administered via intratumoral injection at a dose of $0.5\times10^{12}$ to $1.5\times10^{12}$ vp/day of the oncolytic virus, once daily, consecutively for 4 to 5 days.

In an embodiment according to the present disclosure, the immunostimulant may be administered in combination with one or more other tumor immunological agents including, but not limited to, some interleukin cytokines having immunostimulatory effect, such as IL-1, IL-2, IL-7, IL-12, IL-15, and IL-21; interferons, such as IFN-alpha; colony-stimulating factors, such as G-CSF, and GM-CSF; tumor necrosis factors, such as TNF-alpha; immune cytokines, such as CD40L/CD40; chemokines, such as CCL-3, CCL-5, CCL-26, CX3CL1, CXCL9, and CXCL10; Toll-like receptor (TLR) signal-related molecules; and immune checkpoint related agents, such as anti-PD-1 antibodies and anti-CTLA4 antibodies.

According to the present disclosure, DC proliferation and tumor infiltration can be induced significantly on Day 7 after administration of H101, and enhancing immunity at this time can synergistically promote the immune effect. Therefore, in another embodiment according to the present disclosure, 7-10 days (more preferably, 7 days) after completion of the first course of consecutive administration, the immunostimulant is administered again to carry out an immune-boosting course. The immune-boosting course is performed via intratumoral injection at a dose of $0.5\times10^{12}$ to $1.5\times10^{12}$ vp/day of the oncolytic virus, once daily, consecutively for 1 to 2 days. At an interval of 7-10 days after completion of the immune-boosting course, a following-up immune-boosting course may be performed at the same dose and in the same manner as described above. In this way, the immune-boosting course may be performed 3-4 times.

Hereinafter, the present disclosure will be further explained or described by way of examples, but these examples are not intended to limit the scope of protection of the present disclosure.

EXAMPLES

Unless otherwise specified, all the methods and techniques used in the following examples were carried out in accordance with the conventional operations and conditions in the art.

The materials used in the following examples are described below.

A549 (human non-small cell lung cancer cells) and B16-F0 (mouse melanoma cells) were obtained from the Cell Bank of the Committee on Type Culture Collection of the Chinese Academy of Sciences.

Oncolytic adenovirus, H101, was obtained from Shanghai Sunway Biotech Co., Ltd.

C57BL/6 mice (male, 6-8 weeks old) were obtained from Beijing Vital River Laboratory Animal Technology Co., Ltd. The flow cytometer, D2060R, was obtained from ACEA Biosciences (Hangzhou) Co., Ltd.

Experiments in vitro were repeated at least 3 times, with at least 3 duplicate wells per group for each repetition, and statistical analysis was performed.

Experiments in vivo were performed on at least 5 laboratory animals per group, unless otherwise specified.

Experimental Example 1: Infection of Human and Murine Tumor Cell Lines In Vitro

A549 cells ($3\times10^3$ cells/well) or B16-F0 cells ($4\times10^3$ cells/well) were seeded in a 96-well cell culture plate, and incubated in high-glucose DMEM containing 10% FBS at 37° C. in 5% $CO_2$. After incubation for 12 hours when the cells completely adhered to the wells, H101 (10 MOI for A549 cell line, or 100 MOI for B16-F0 cell line) was added, and the cells were further incubated for 12 hours. Then, the medium was replaced with a fresh one. The time point at which the virus was added was taken as 0 hour. MTT assay was performed every 24 hours (MTT reagent was purchased from Sigma-Aldrich; Item No. M5655-1G). The control group was carried out in complete medium without the addition of any oncolytic virus.

Figure 1B:
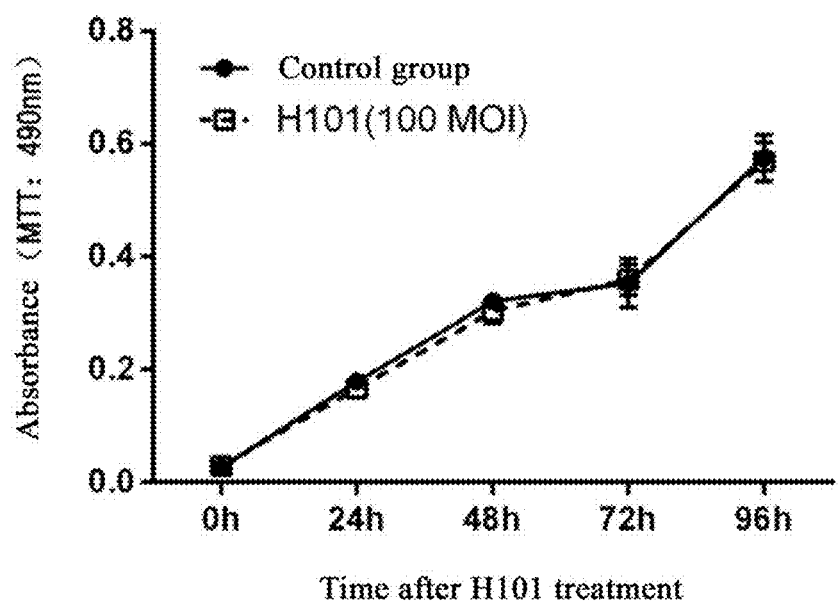
FIG. 1B shows the results of B16-F0 cells infected with H101.

From Day 3 after infection of A549 cells by H101, the MTT results showed that the amount of viable cells was drastically reduced and it was observed under the microscope that a large number of cells were dead and disrupted, indicating that H101 infection in vitro can directly kill human tumor cell lines and promote the release of tumor antigens (as shown in FIG. 1A). However, direct inhibition of the proliferation of murine B16-F0 cells was not observed, even though the infective dose MOI was increased 10-fold (as shown in FIG. 1B).

Experimental Example 2: Effective Promotion of the Release of Tumor Antigens from Murine Tumor Cell Line In Vivo To study the immunological effects of H101, the present inventors developed an animal model bearing murine melanoma subcutaneously and verified the in vitro cytotoxicity of H101 to the melanoma cell line (B16-F0) in advance. The results demonstrated that the direct killing effect of H101 on the murine B16-F0 cell line was extremely weak due to the species specificity of the human adenovirus type 5 infection (see FIG. 1B of Experimental example 1). The model was in line with the research purpose of studying the immunostimulant effect of H101 while ruling out the direct oncolytic effect thereof as far as possible. Thereafter, the promoting effect of H101 on apoptosis and complete antigen release of the cell line (B16-F0) in the animal model was investigated.

For tumor bearing, B16-F0 cells ($2 \times 10^6$ cells/100 μl DMEM) were injected into the right back of C57BL/6 male mice at a dose of 100 μl per animal. On the $7^{th}$ day of tumor-bearing when the tumor volume reached about 150 mm$^3$, for the experimental group, H101 at a dose of $2 \times 10^{10}$ vp/50 μl pH7.4 PBS (PBS reagent was purchased from Sangon Biotech (Shanghai) Co., Ltd., Item No. B548117) was intratumorally injected, once daily for 4 consecutive days; meanwhile for the control group, 50 μl PBS was intratumorally injected, once daily for 4 consecutive days. The first day of the administration was taken as Day 0. Then, on Days 3, 7, and 13, the mice were sacrificed and tumors were taken to perform immunohistochemistry (IHC) detection of Caspase-3 (using anti-mouse Caspase-3 antibody, purchased from R&D Systems, Item No. AF-605-NA) and HE staining (using Hematoxylin-Eosin (HE) staining kit, purchased from Sangon Biotech (Shanghai) Co., Ltd., Item No. E607318).

Figure 2A:
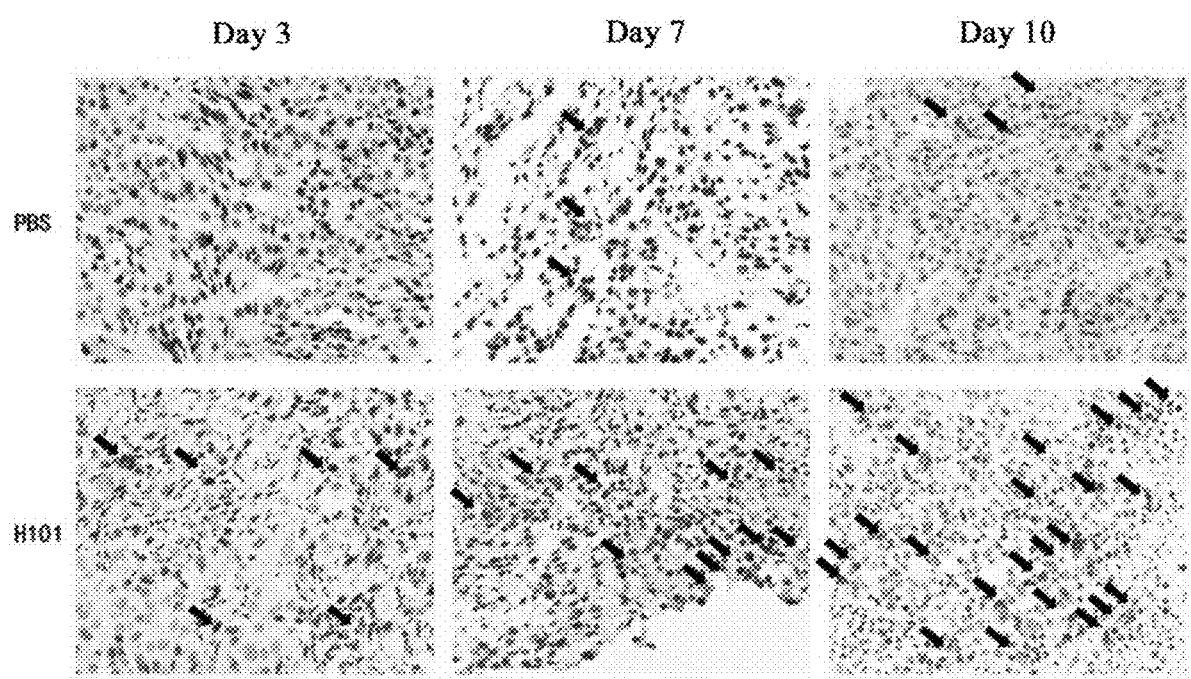
FIG. 2A shows the immunohistochemical results of tumor antigen release, in which the arrows indicate the positive sites of the immunohistochemistry of Caspase-3 protein.
Figure 2B:
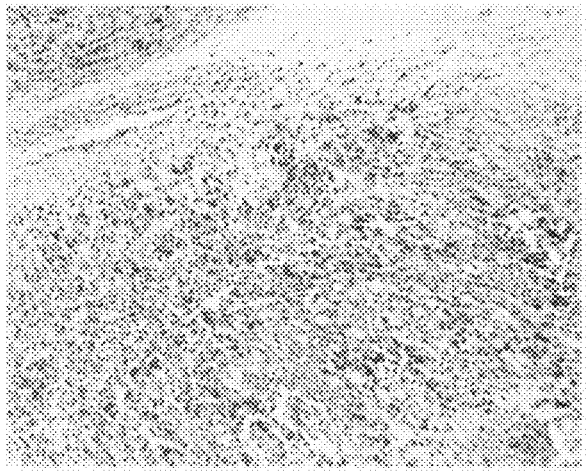
FIG. 2B shows the HE staining results of cell lysis, in which the upper and lower images on the left were taken from different parts of the PBS group sample, while the upper and lower images on the right were taken from different parts of the H101 group sample, with the arrows indicating the cell lysis sites.
Figure 2B:
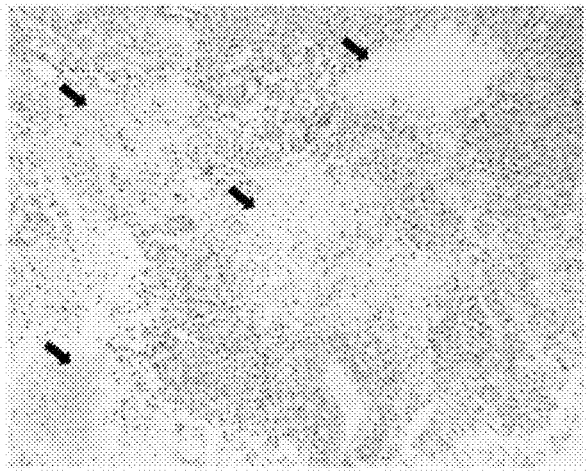
Figure 2B:
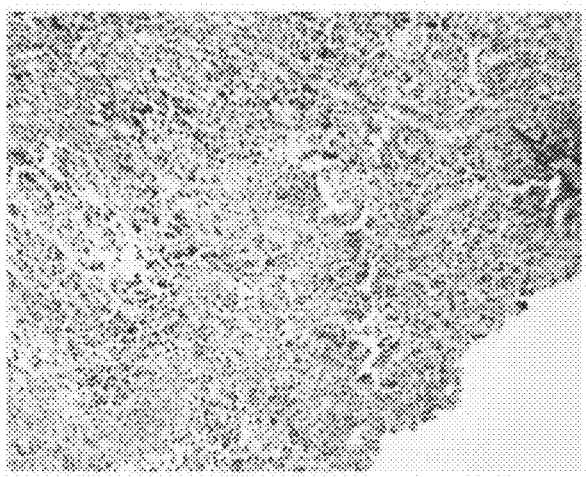
Figure 2B:
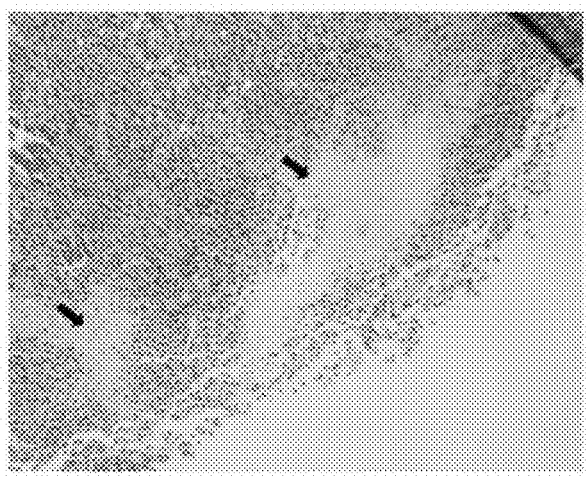

The IHC results demonstrated that Caspase-3 was mainly expressed in the nucleus. In the H101 group, the expression amounts of Caspase-3 on Day 7 and Day 10 were significantly higher than that on Day 3. Also, on Day 7 and Day 10, the counts of Caspase-3 protein-positive cells in the H101 experimental group were significantly higher than that in the PBS control group (as shown in FIG. 2A), and significant cell lysis was observed only on Day 13 (as shown in FIG. 2B). Caspase-3 is the main indicator of apoptosis, and cell lysis is an important manifestation of immunogenic cell death. Therefore, this experiment indicates that the oncolytic virus can induce apoptosis and further induce immunogenic cell death, thereby effectively promoting the release of tumor antigens.

Experimental Example 3: Stimulation of the Immune System and Activation of Dendritic Cells (DCs)

For tumor bearing, B16-F0 cells ($2 \times 10^6$ cells/100 μl DMEM) were injected into the right back of C57BL/6 male mice at a dose of 100 μl per animal. On the 7th day of tumor-bearing, for the experimental group, H101 ($1 \times 10^{10}$ vp/60 μl PBS) was intratumorally injected once for one day; meanwhile for the control group, 60 μl PBS was intratumorally injected once for one day. The first day of the administration was taken as Day 0. Then, on Days 1, 3 and 7, the mice were sacrificed and spleens were taken to perform flow cytometry detection of DCs (using anti-mouse CD11b-FITC and CD11c-APC antibodies which were purchased from eBioscience, Item Nos. 11-0112-85 and 17-0114-81). The results are shown in FIG. 3A.

For tumor bearing, B16-F0 cells ($2 \times 10^6$ cells/100 μl DMEM) were injected into the right back of C57BL/6 male mice at a dose of 100 μl per animal. On the $7^{th}$ day of tumor-bearing, for the experimental group, H101 ($5 \times 10^9$ vp/50 μl PBS) was intratumorally injected, once daily for 4 consecutive days; meanwhile for the control group, 50 μl PBS was intratumorally injected, once daily for 4 consecutive days. The first day of the administration was taken as Day 0. Then, on Day 12, the mice were sacrificed and spleens were taken to perform flow cytometry detection of DCs (anti-mouse CD80-APC, CD11b-FITC and CD11c-APC antibodies were purchased from eBioscience, Item Nos. 17-0801-82, 11-0112-85 and 17-0114-81; anti-mouse CD86-FITC antibody was purchased from BD Pharmingen, Item No. 561962). The results are shown in FIGS. 3B, 3C and 3D, respectively.

Figure 3A:
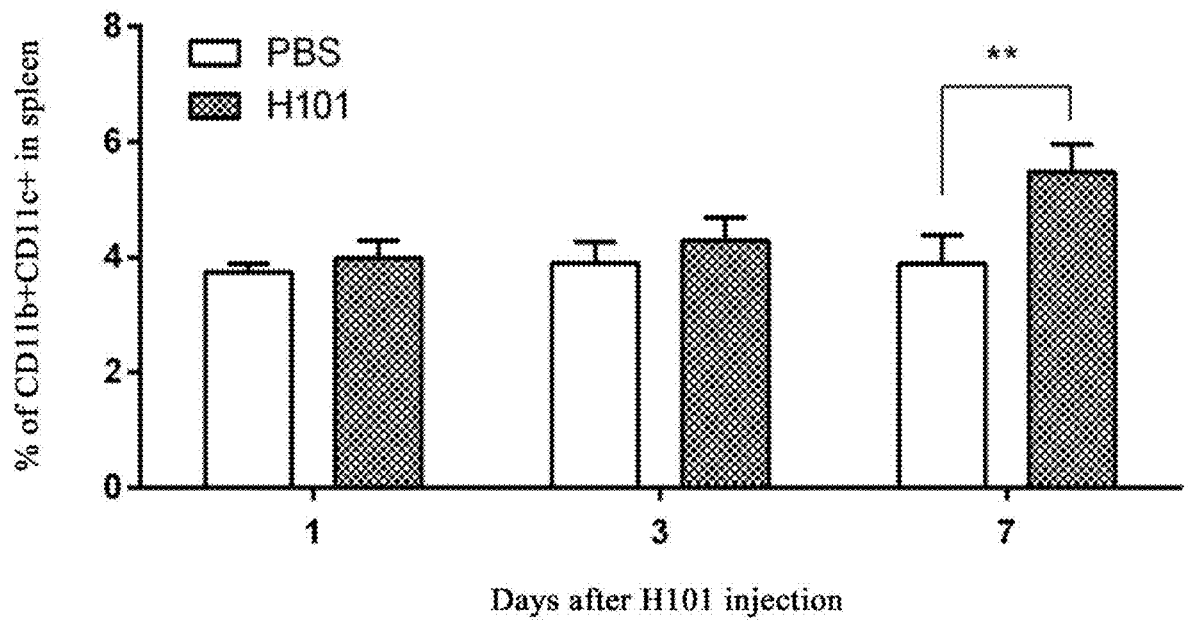
FIG. 3A shows the flow cytometry results of immature DC cells on Days 1, 3 and 7 after administration of H101, in which the ordinate represents the percentage (%) of $CD11b^+CD11c^+$ double positive cells in the spleen, and the abscissa represents Days after H101 injection.
Figure 3B:
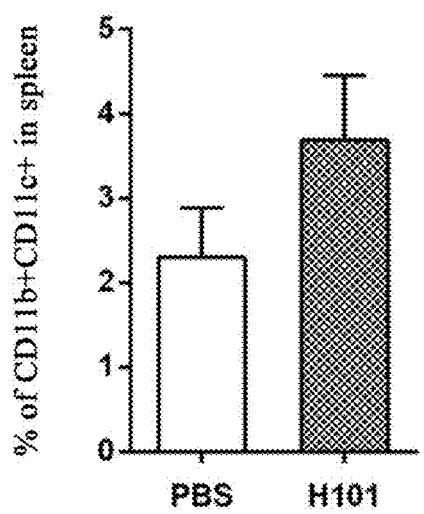
FIG. 3B shows the flow cytometry results of immature DC cells on Day 12 after administration of H101, in which the ordinate represents the percentage (%) of $CD11b^+CD11c^+$ double positive cells in the spleen.
Figure 3C:
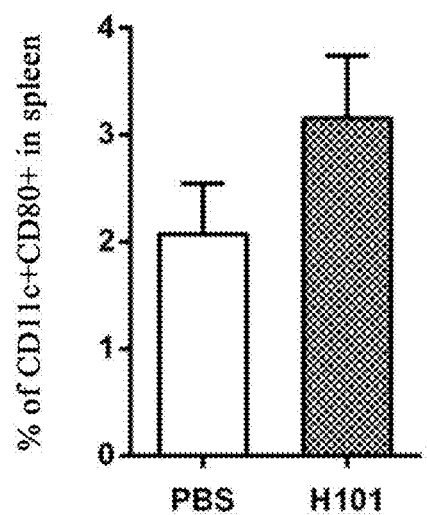
FIGS. 3C-3D show the flow cytometry results of mature DC cells on Day 12 after administration of H101, in which the ordinate of FIG. 3C represents the percentage (%) of $CD11c^+CD80^+$ double positive cells in the spleen, and the ordinate of FIG. 3D represents the percentage (%) of $CD11c^+CD86^+$ double positive cells in the spleen.
Figure 3D:
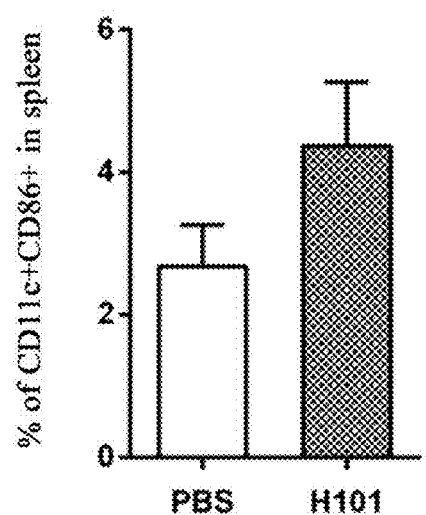

The laboratory animals after administration of H101 were monitored continuously, and it was found that immature DCs in the peripheral blood represented by the spleen were significantly up-regulated from Day 7 after the administration (FIG. 3A). On Day 12 after the administration, immature DCs (CD11b$^+$CD11c$^+$) and mature DCs (CD11c$^+$CD80$^+$ or CD11c$^+$CD86$^+$) in the spleens of the animals still showed an up-regulated trend (FIGS. 3B-3D).

Experimental Example 4: Stimulation of the Immune System and Activation of T Cells For tumor bearing, B16-F0 cells ($1.5 \times 10^6$ cells/100 μl DMEM) were injected into the right back of C57BL/6 male mice at a dose of 100 μl per animal. On the $7^{th}$ day of tumor-bearing, for the experimental group, H101 ($4 \times 10^9$ vp/50 μl PBS) was intratumorally injected, once daily for 4 consecutive days; meanwhile for the control group, 50 μl PBS was intratumorally injected, once daily for 4 consecutive days. The first day of the administration was taken as Day 0. Then, on Day 7, the mice were sacrificed and spleens were taken to perform flow cytometry detection of T lymphocytes (anti-mouse CD3e PE-Cyanine7 antibody was purchased from eBioscience, Item No. 35-0031-82; anti-mouse CD4-FITC and CD8-APC antibodies were purchased from BD Pharmingen, Item Nos. 553729 and 553035). The results are shown in FIGS. 4A, 4B and 4C, respectively.

For tumor bearing, B16-F0 cells ($2 \times 10^6$ cells/100 μl DMEM) were injected into the right back of C57BL/6 male mice at a dose of 100 μl per animal. On the 7th day of tumor-bearing, for the experimental group, H101 ($1\times10^{10}$ vp/60 µl PBS) was intratumorally injected once for one day; meanwhile for the control group, 60 µl PBS was intratumorally injected once for one day. The first day of the administration was taken as Day 0. Then, on Day 10, the mice were sacrificed and spleens were taken to perform T lymphocytes typing by the flow cytometric detection (using anti-mouse CD3e PE-Cyanine7 antibody, purchased from eBioscience, Item No. 35-0031-82). The results are shown in FIG. 4D.

Figure 4A:
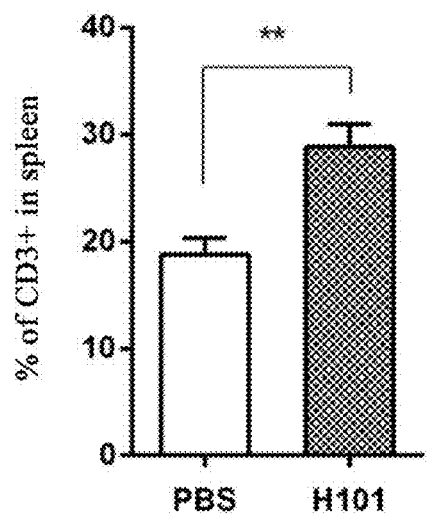
FIGS. 4A-4C show the flow cytometry results of $CD3^+$, $CD4^+$ and $CD8^+$ T cells on Day 7 after administration of H101, respectively, in which the ordinate of FIG. 4A represents the percentage (%) of $CD3^+$ positive cells in the spleen, the ordinate of FIG. 4B represents the percentage (%) of $CD3^+CD4^+CD8^-$ cells in the spleen, and the ordinate of FIG. 4C represents the percentage (%) of $CD3^+CD4^-CD8^+$ cells in the spleen.
Figure 4B:
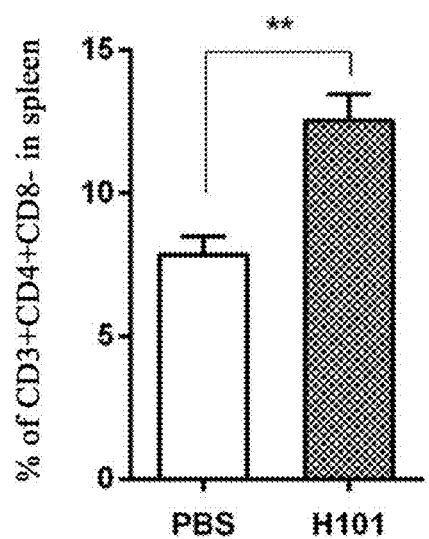
Figure 4C:
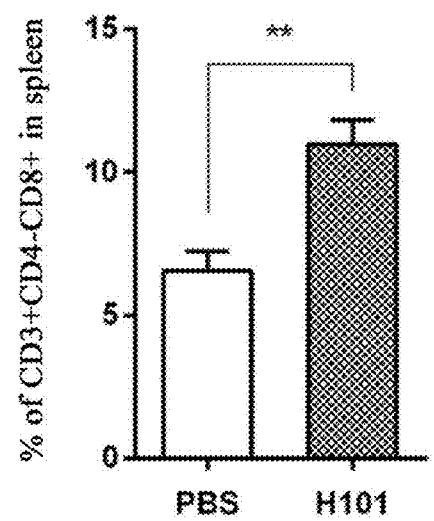
Figure 4D:
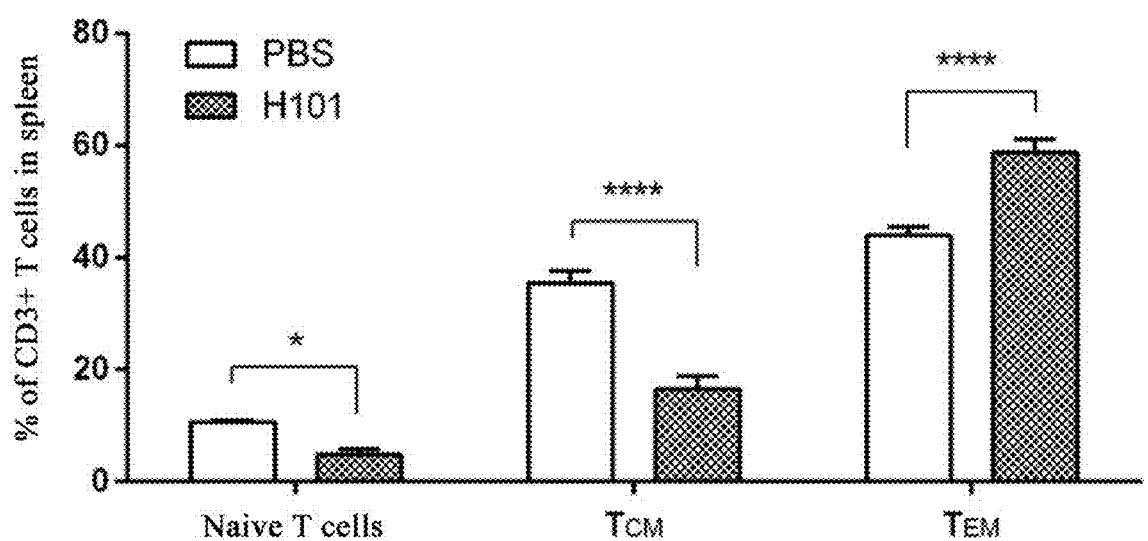
FIG. 4D shows the results of T lymphocytes typing by flow cytometry on Day 10 after administration of H101, in which the ordinate represents the percentage (%) of $CD3^+$ T cells in the spleen.

On Day 7 after administration of H101, the $CD3^+$, $CD4^+$ and $CD8^+$ T cells in the spleens were significantly up-regulated (FIGS. 4A-4C). On Day 10, T cell subtype analysis (anti-mouse CD4-FITC and CD8-APC antibodies were purchased from BD Pharmingen, Item Nos. 553729 and 553035; anti-mouse CD44-PE and CD62L-APC antibodies were purchased from eBioscience, Item Nos. 12-0441-83 and 17-0621-82) indicated that in the $CD3^+$ T cell population, Naive T ($CD44^{low}$ $CD62L^{hi}$) cells and Tcm (central memory T cells, $CD44^{hi}$ $CD62L^{hi}$) of the laboratory animals in the H101-administered group were down-regulated, while Tem (effector memory T cells, $CD44^{hi}$ $CD62L^{low}$) was up-regulated, indicating that T cell immunity was mobilized and activated in the body (FIG. 4D).

Figure 5:
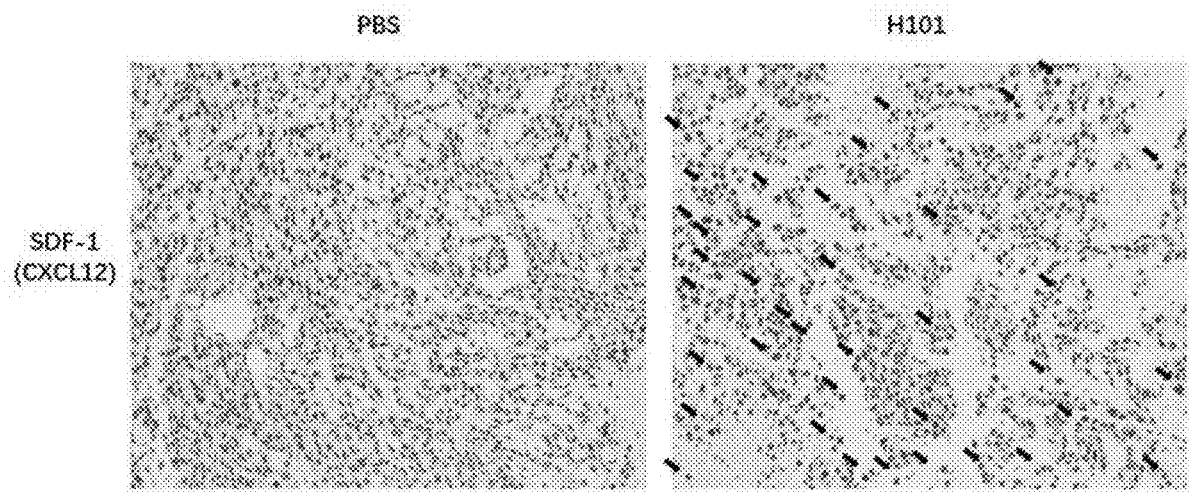
FIG. 5 shows the results of expression of the chemokine CXCL12 in Experimental example 5 according to the present disclosure, in which the arrows indicate the positive sites of immunohistochemistry of CXCL12 protein.

Experimental Example 5: Intratumoral Administration Stimulates the Expression of Chemokine CXCL12 at Tumor Site, which Facilitates the Homing and Aggregation of Immune Cells at the Tumor Site For tumor bearing, B16-F0 cells ($1\times10^6$ cells/100 µl DMEM) were injected into the right back of C57BL/6 male mice at a dose of 100 µl per animal. On the $7^{th}$ day of tumor-bearing, for the experimental group, H101 ($4\times10^9$ vp/50 µl PBS) was intratumorally injected, once daily for 4 consecutive days; meanwhile for the control group, 50 µl PBS was intratumorally injected, once daily for 4 consecutive days. The first day of the administration was taken as Day 0. Then, on Day 13, the mice were sacrificed and tumors were taken to perform IHC detection of the chemokine CXCL12 (using anti-mouse CXCL12 antibody, purchased from Abcam, Item No. AB25117). The results are shown in FIG. 5.

The IHC results demonstrated that the expression of the chemokine CXCL12 in tumor site was up-regulated on Day 13 after administration of H101. The up-regulation of the chemokine can promote vascular proliferation, improve the permeability of tumor entities, and facilitate the homing and aggregation of immune cells at the tumor site.

Experimental Example 6: Intratumoral Injection of Oncolytic Virus Promotes the Infiltration of NKs, DCs and CTLs into Tumor Entities For tumor bearing, B16-F0 cells ($2\times10^6$ cells/100 µl DMEM) were injected into the right back of C57BL/6 male mice at a dose of 100 µl per animal. On the 7th day of tumor-bearing when the tumor volume reached about 150 $mm^3$, for the experimental group, H101 ($2\times10^{10}$ vp/50 µl PBS) was intratumorally injected, once daily for 4 consecutive days; meanwhile for the control group, 50 µl PBS was intratumorally injected, once daily for 4 consecutive days. The first day of the administration was taken as Day 0. Then, on Days 3, 7 and 10, the mice were sacrificed and tumors were taken to perform flow cytometric analysis (anti-mouse CD314 (NKG2D)-APC, NK1.1-FITC, CD107a-PE, CD3e PE-Cyanine7, MHC Class I (H-2Kd)-PE and MHC Class II (I-A/I-E)-PE-Cyanine7 antibodies were purchased from eBioscience, Item Nos. 17-5882-82, 11-5941-85, 12-1071-83, 35-0031-82, 12-5957-82 and 25-5321-82; anti-mouse CD4-FITC and CD8-APC antibodies were purchased from BD Pharmingen, Item Nos. 553729 and 553035; anti-mouse CD11b-FITC and CD11c-APC antibodies were purchased from eBioscience, Item Nos. 11-0112-85 and 17-0114-81). The results are shown in FIG. 6.

Figure 6A:
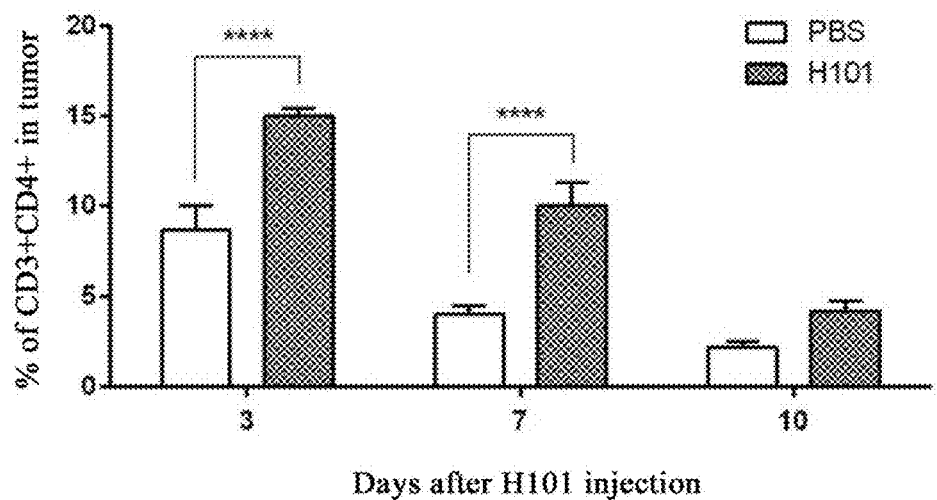
FIGS. 6A and 6B show the flow cytometry results of $CD4^+$ T cells and the $CD4^+$ T cells in secretory activation state after administration of H101, respectively, in which the ordinate of FIG. 6A represents the percentage (%) of $CD3^+CD4^+$ double positive cells in the tumor, the ordinate of FIG. 6B represents the percentage (%) of $CD4^+CD107^+$ double positive cells in the tumor, and the abscissas thereof both represent Days after H101 injection.
Figure 6B:
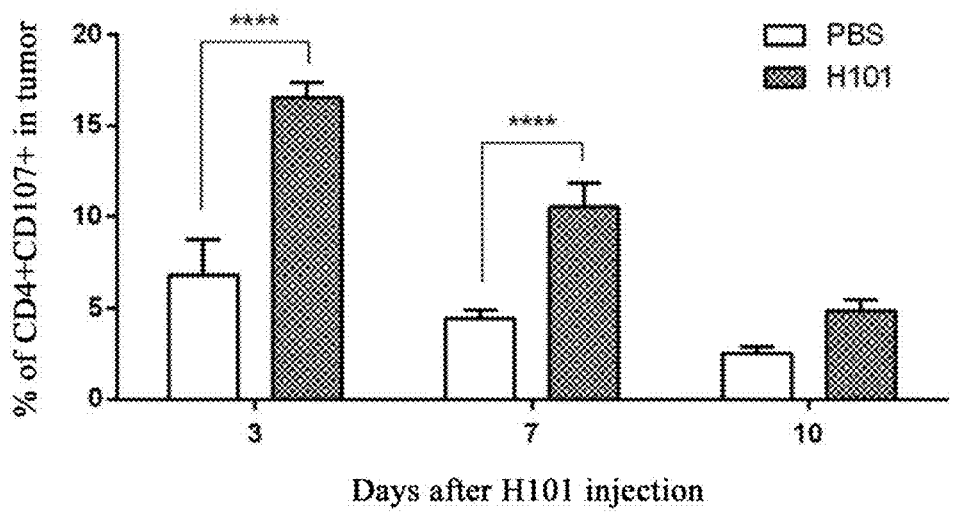
Figure 6C:
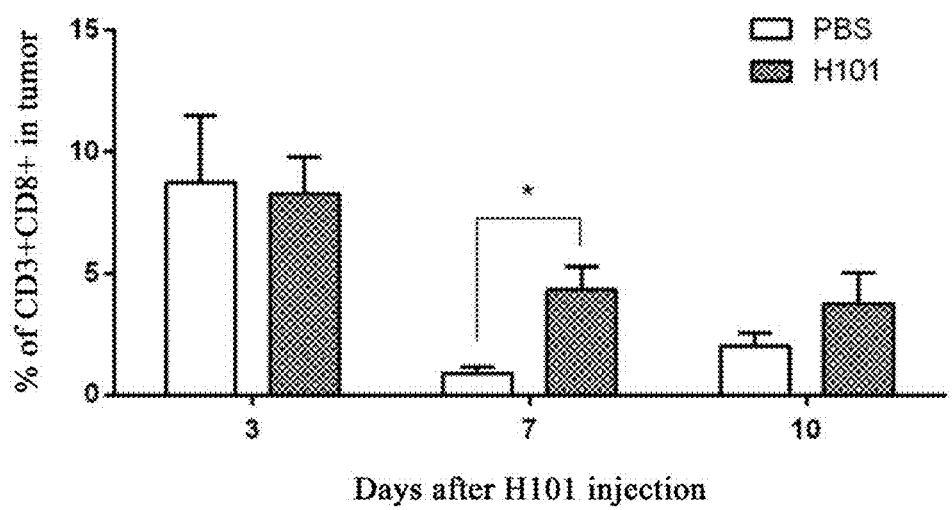
FIGS. 6C and 6D show the flow cytometry results of CD8+ T cells and the CD8+ T cells in secretory activation state after administration of H101, respectively, in which the ordinate of FIG. 6C represents the percentage (%) of CD3+CD8+ double positive cells in the tumor, the ordinate of FIG. 6D represents the percentage (%) of CD8+CD107+ double positive cells in the tumor, and the abscissas thereof both represent Days after H101 injection.
Figure 6D:
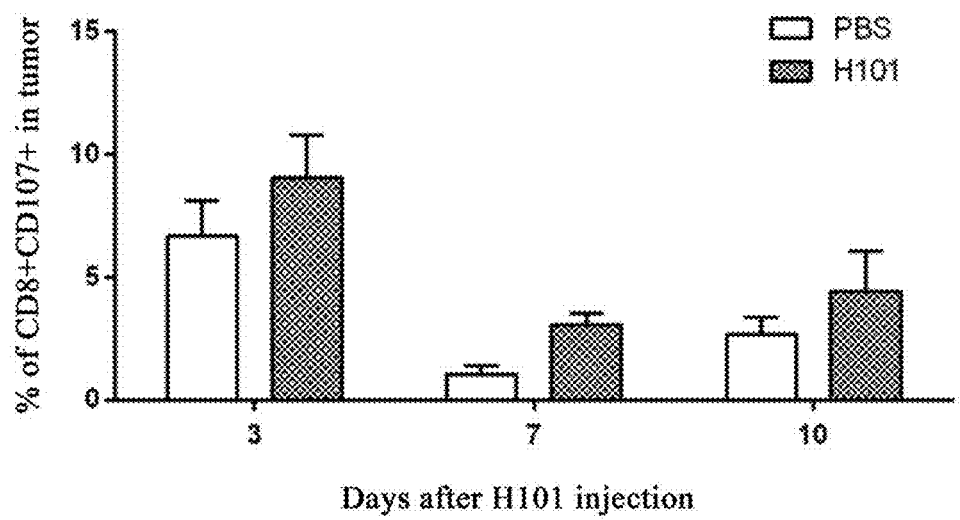
Figure 6E:
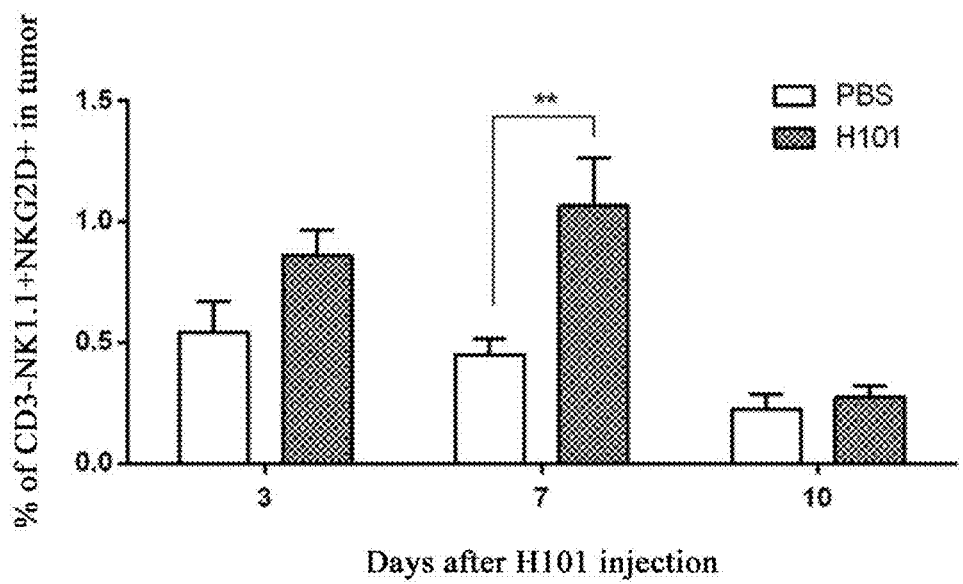
FIG. 6E shows the flow cytometry results of NK cells after administration of H101, in which the ordinate represents the percentage (%) of CD3−NK1.1+NKG2D+ cells in the tumor, and the abscissa represents Days after H101 injection.
Figure 6F:
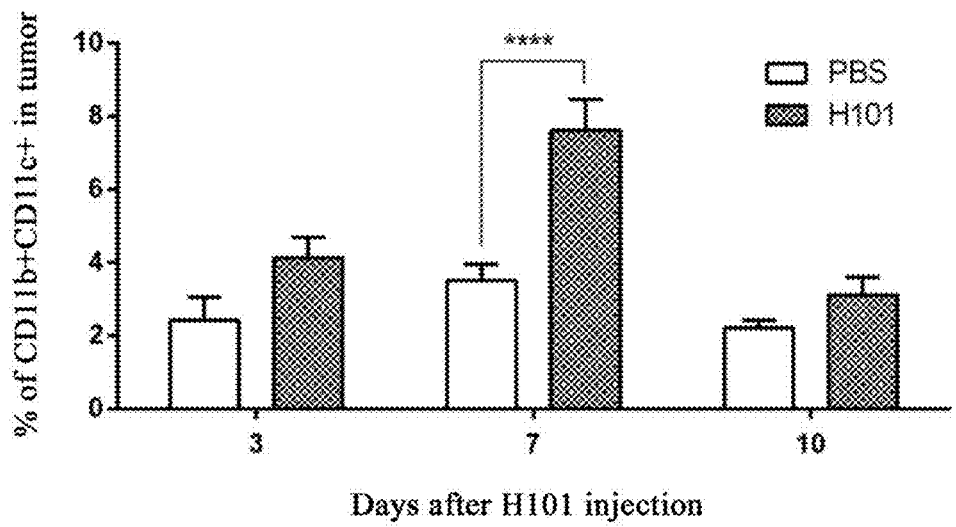
FIG. 6F shows the flow cytometry results of immature DC cells after administration of H101, in which the ordinate represents the percentage (%) of CD11b+ CD11c+ double positive cells in the tumor, and the abscissa represents Days after H101 injection.
Figure 6G:
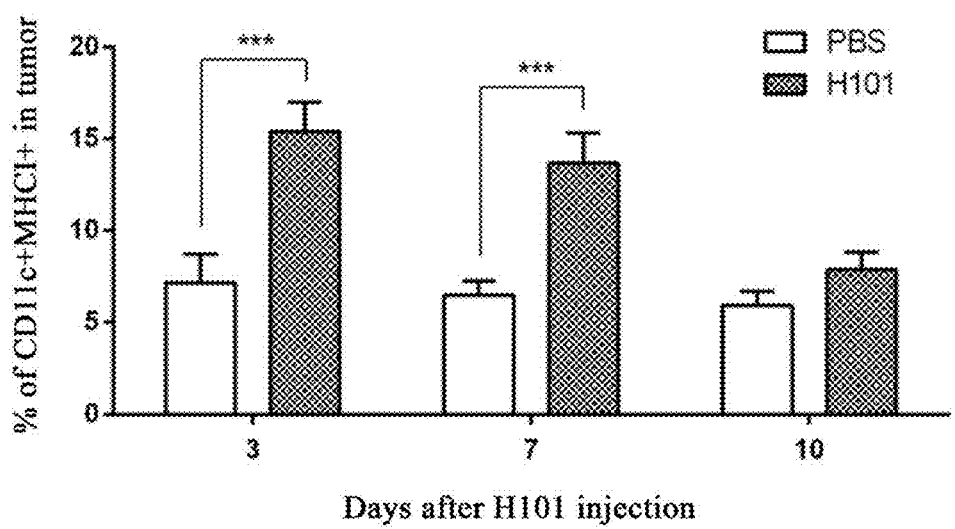
FIGS. 6G and 6H show the flow cytometry results of mature DC cells after administration of H101, in which the ordinate of FIG. 6G represents the percentage (%) of CD11c+MHCI+ double positive cells in the tumor, the ordinate of FIG. 6H represents the percentage (%) of CD11c+MHCII+ double positive cells in the tumor, and the abscissas thereof both represent days after H101 injection.
Figure 6H:
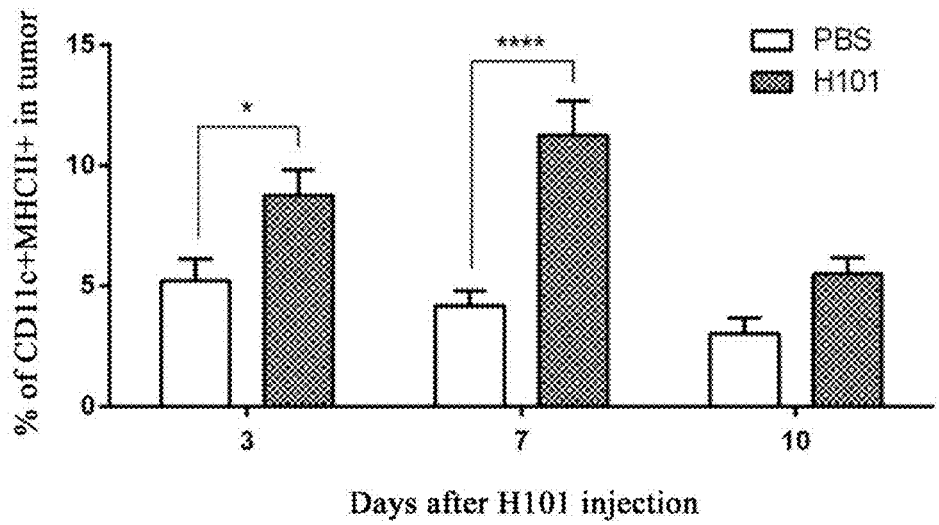

On Day 3 and Day 7 after administration of H101, $CD4^+$ T cells and the $CD4^+$ T cells in secretory activation state ($CD4^+CD107a^+$) in tumor tissues were significantly up-regulated (FIGS. 6A and 6B), while $CD8^+$ T cells were significantly up-regulated on Day 7. Also, on Day 7 and Day 10, $CD8^+$ T cells and the $CD8^+$ T cells in secretory activation state ($CD8^+CD107a^+$) showed an up-regulated trend (FIGS. 6C and 6D). On Day 7 after the administration, NK cells were significantly up-regulated (FIG. 6E). Meanwhile, immature DCs ($CD11b^+CD11c^+$) in the tumors were significantly up-regulated on Day 7, while mature DCs ($CD11c^+MHCI^+$ or $CD11c^+MHCII^+$) were significantly up-regulated on Day 3 and Day 7 (FIGS. 6F-6H).

Figure 7A:
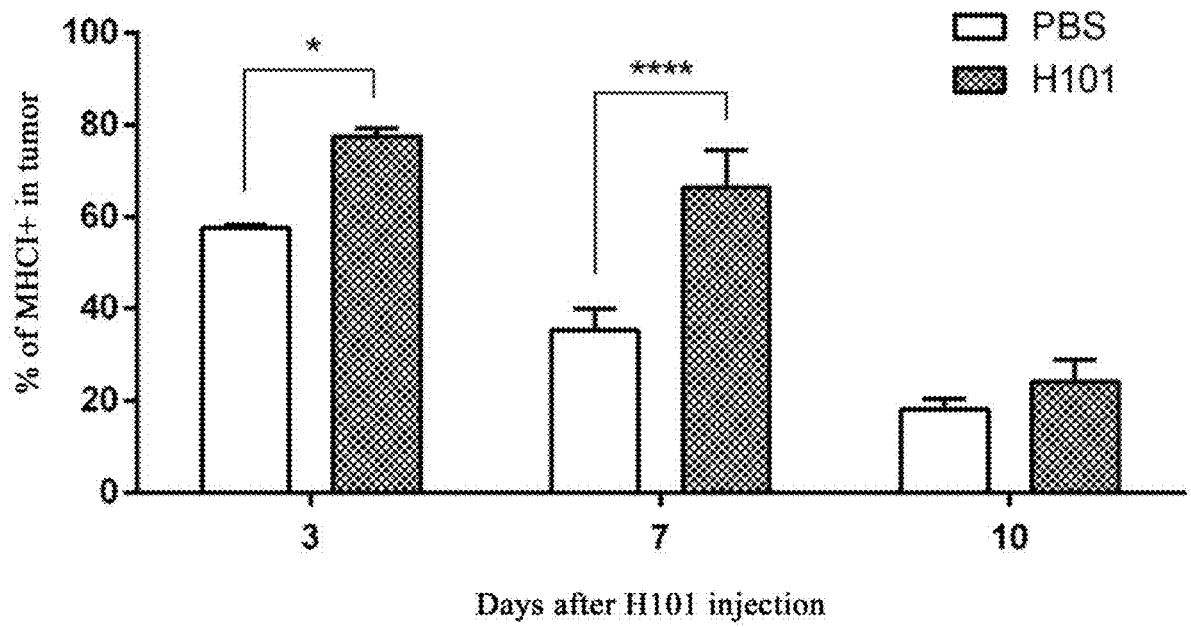
FIG. 7A shows the flow cytometry results of MHC-I molecule-expressing cells, in which the ordinate represents the percentage (%) of MHCI+ positive cells in the tumor, and the abscissa represents Days after H101 injection.
Figure 7B:
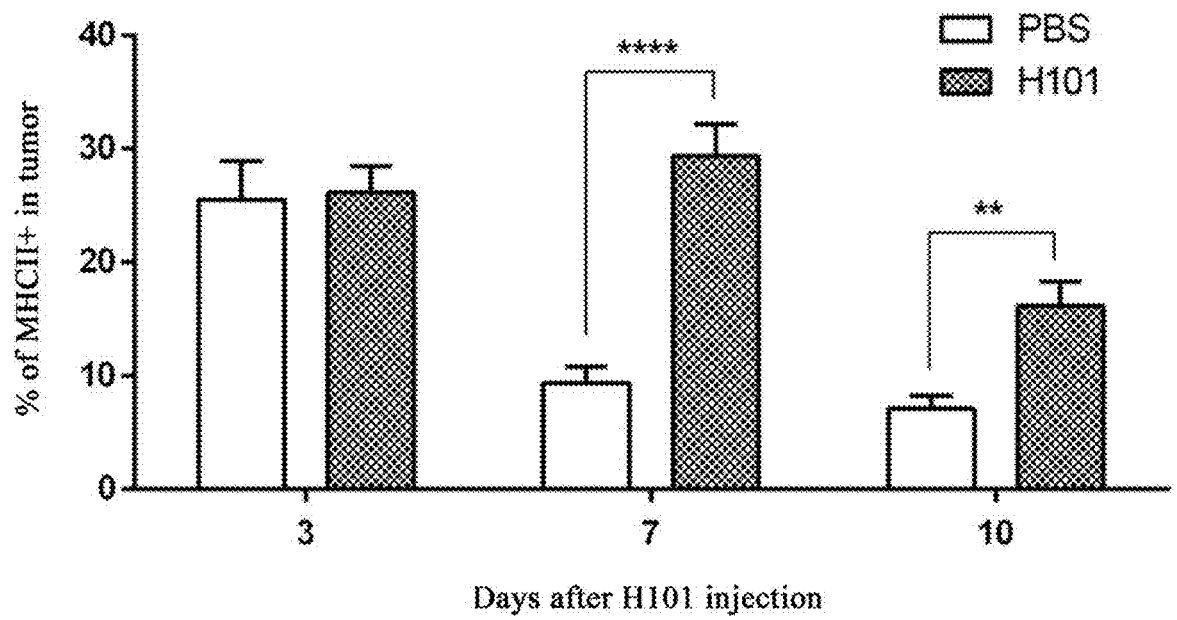
FIG. 7B shows the flow cytometry results of MHC-II molecule-expressing cells, in which the ordinate represents the percentage (%) of MHCII+ positive cells in the tumor, and the abscissa represents Days after H101 injection.

Experimental Example 7: Injection Stimulates MHCI/II Expression of Tumor Cells and Enhances Immune Recognition For tumor bearing, B16-F0 cells ($2\times10^6$ cells/100 µl DMEM) were injected into the right back of C57BL/6 male mice at a dose of 100 µl per animal. From the 7th day of tumor-bearing when the tumor volume reached about 150 $mm^3$, for the experimental group, H101 ($2\times10^{10}$ vp/50 µl PBS) was intratumorally injected for 4 consecutive days; meanwhile for the control group, 50 µl PBS was intratumorally injected for 4 consecutive days. The first day of the administration was taken as Day 0. Then, on Days 3, 7 and 10, the mice were sacrificed and tumors were taken to perform flow cytometric analysis (anti-mouse MHC Class I (H-2Kd)-PE and MHC Class II (I-A/I-E)-PE-Cyanine7 antibodies were purchased from eBioscience, Item Nos. 12-5957-82 and 25-5321-82). The results are shown in FIGS. 7A and 7B.

On Day 3 and Day 7 after administration of H101, the percentages of MHC-I molecule-expressing cells in the tumor site were significantly up-regulated. On Day 7 and Day 10, the percentages of MHC-II molecule-expressing cells were significantly up-regulated. The up-regulation of the expression of the MHC molecules strongly promotes the tumor immune recognition response and improves the killing efficiency of immune cells.

Experimental Example 8: Relative Inhibition of Tumor Growth in Laboratory Animals For tumor bearing, B16-F0 cells ($2\times10^6$ cells/100 µl DMEM) were injected into the right back of C57BL/6 male mice at a dose of 100 µl per animal. On the 7th day of tumor-bearing when the tumor volume reached about 150 $mm^3$, for the experimental group, H101 ($2\times10^{10}$ vp/50 µl PBS) was intratumorally injected, once daily for 4 consecutive days; meanwhile for the control group, 50 µl PBS was intratumorally injected, once daily for 4 consecutive days. The first day of the administration was taken as Day 0. Tumor sizes were measured every 2 days, and on Days 3, 7 and 10, the mice were sacrificed and tumors were taken to weigh. The results are shown in FIG. 8.

Figure 8A:
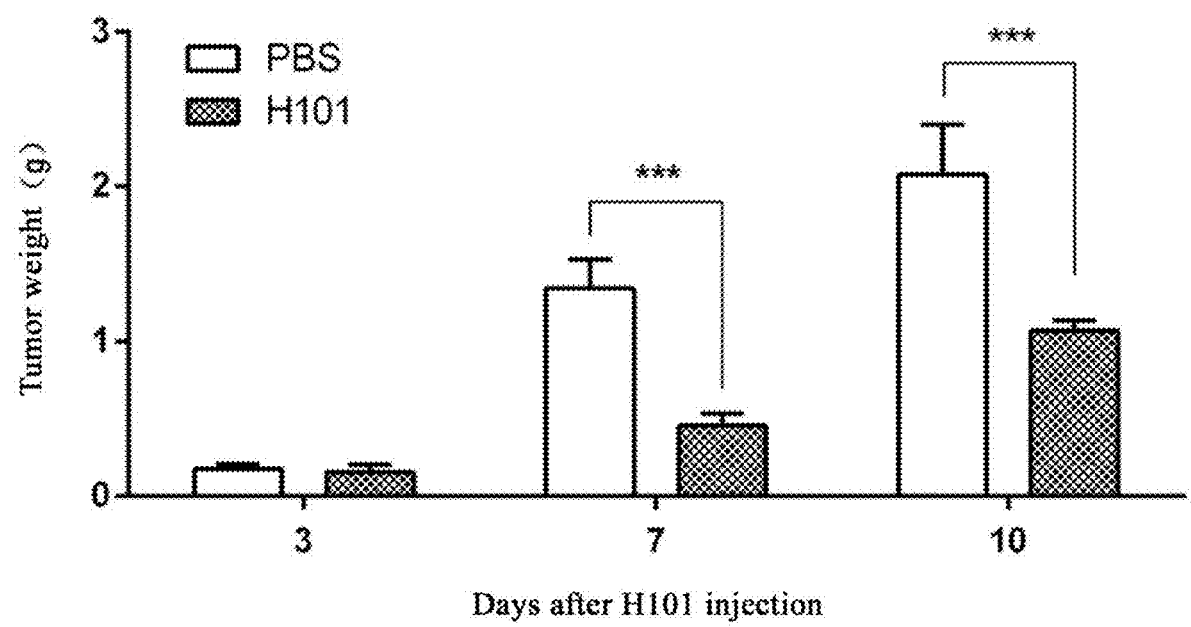
FIG. 8A shows the results of tumor weight over time.
Figure 8B:
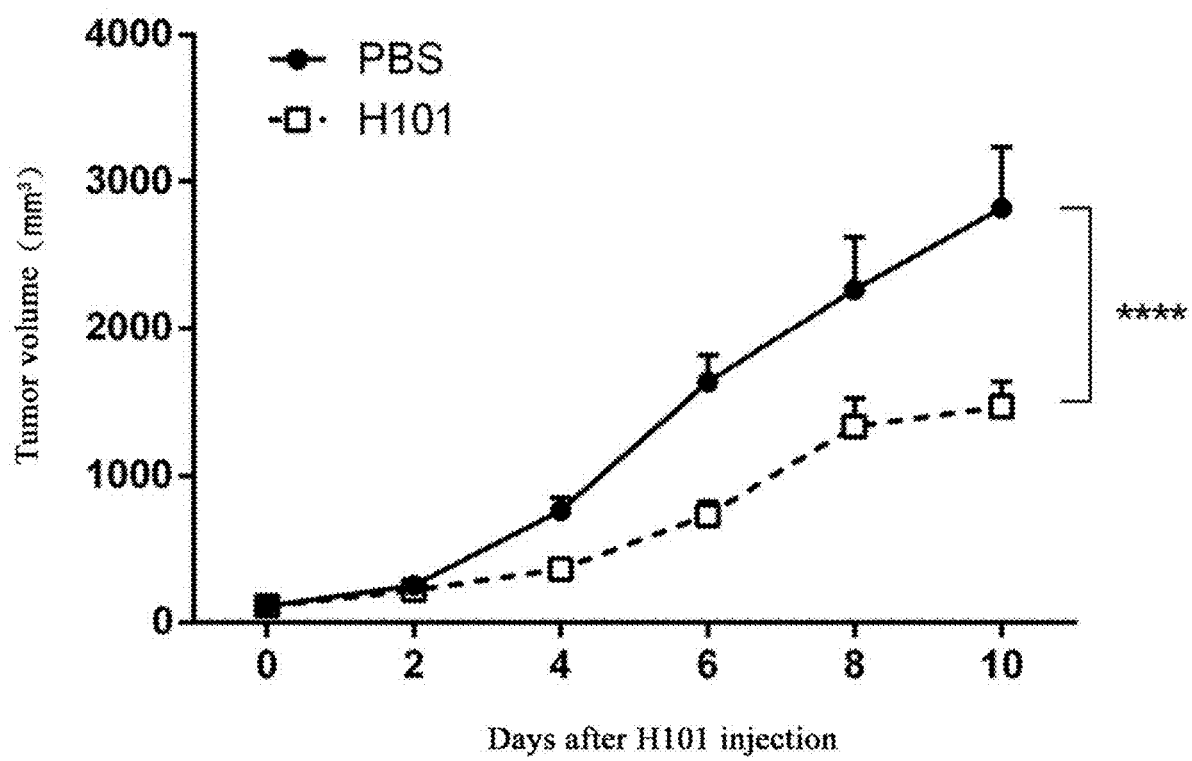
FIG. 8B shows the results of tumor volume over time.
Figure 8C:
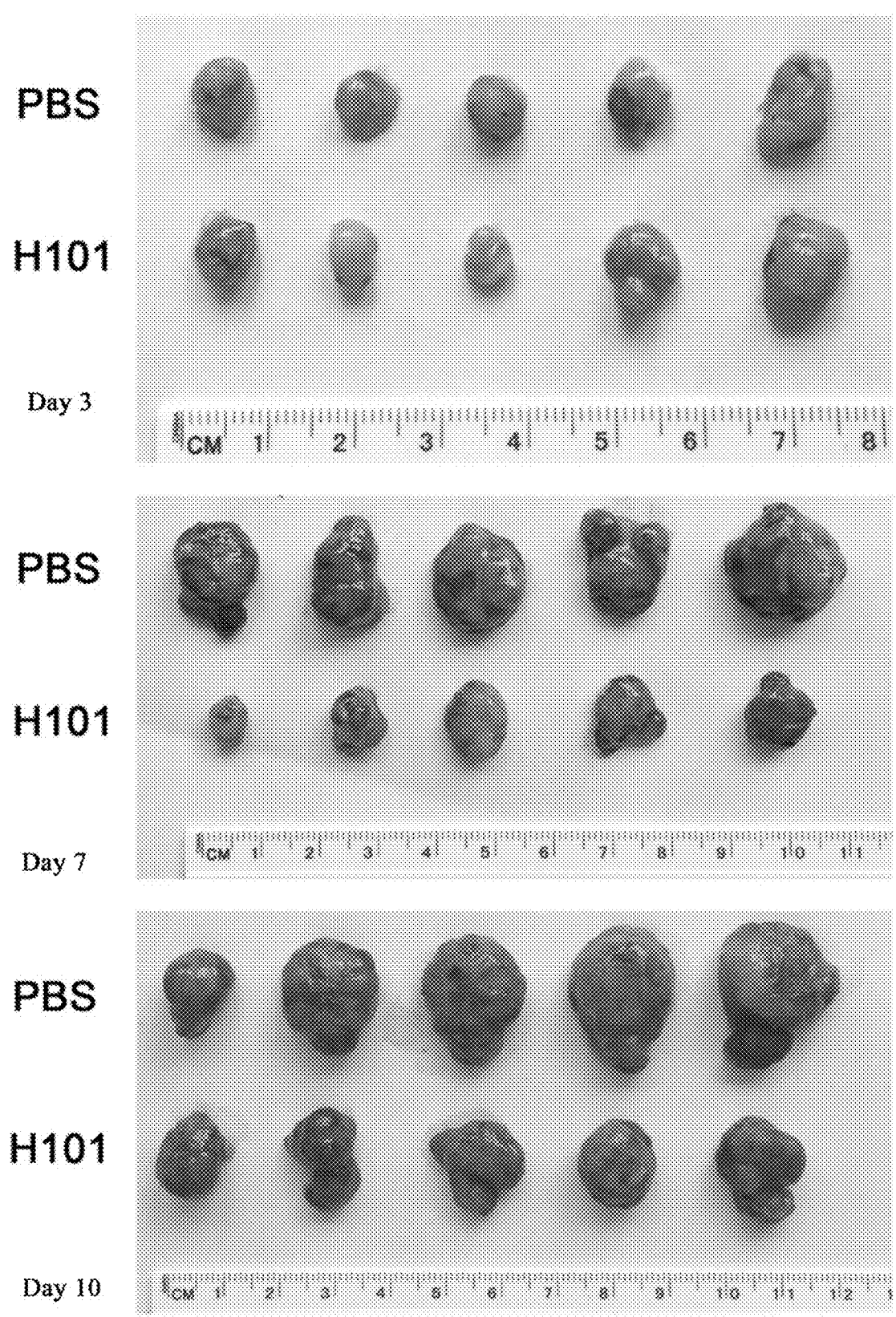
FIG. 8C is a photograph showing tumor size over time.

Compared with the control group, from Day 7 after the administration of H101, the tumor volumes of the animals were significantly smaller than those of the PBS-injected control group, and the difference was significant (FIGS. 8A-8C).

Figure 9:
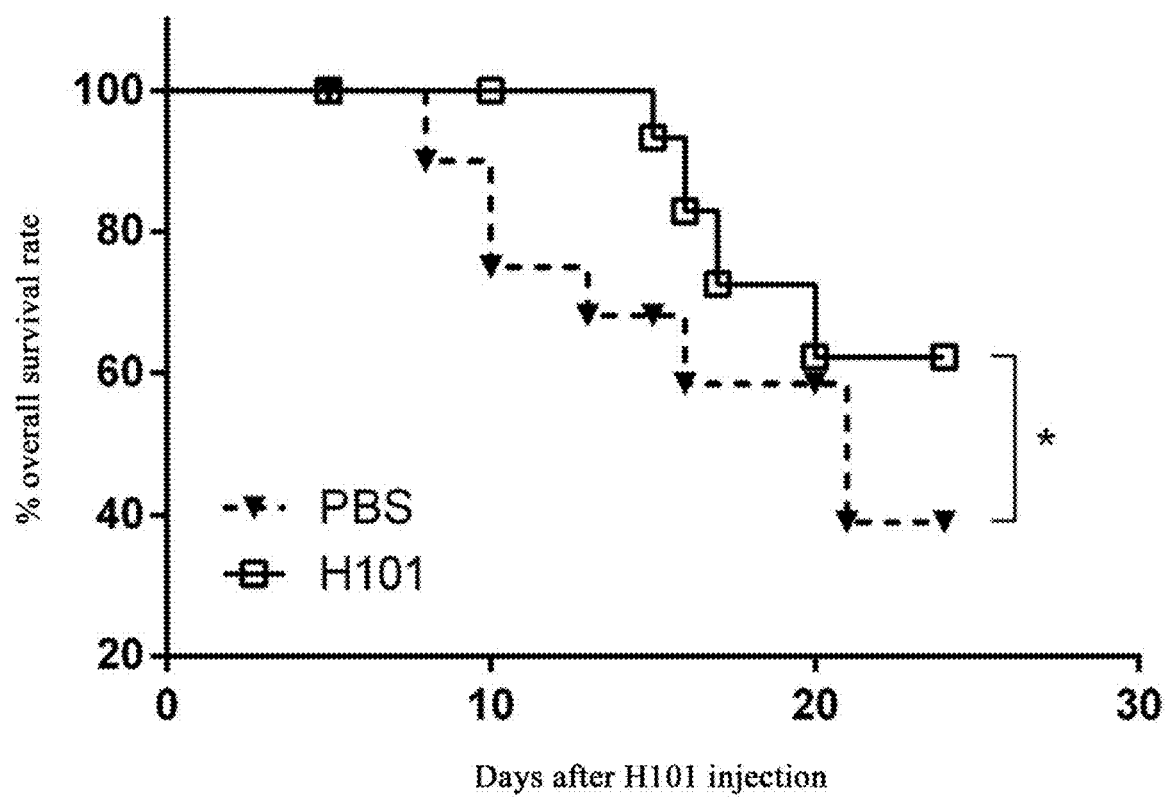
FIG. 9 shows the results of H101 improving the overall survival rate of laboratory animals in Experimental example 9 according to the present disclosure.

Experimental Example 9: Increasing of the Overall Survival Rate of Laboratory Animals For tumor bearing, B16-F0 cells ($2\times10^6$ cells/100 μl DMEM) were injected into the right back of C57BL/6 male mice at a dose of 100 μl per animal. On the $7^{th}$ day of tumor-bearing, for the experimental group, H101 ($4\times10^9$ vp/50 μl PBS) was intratumorally injected, once daily for 4 consecutive days; meanwhile for the control group, 50 μl PBS was intratumorally injected, once daily for 4 consecutive days. The survival status of the mice was observed every day. The results are shown in FIG. 9.

The experiment of survival rate demonstrated that administering H101 can significantly prolong the overall survival rate of laboratory animals.

Although in the in vitro killing experiment the proliferation of the murine B16-F0 cell line was almost unaffected by H101, the results of the in vivo administration demonstrated that administering H101 can significantly inhibit the tumor growth in laboratory animals relative to the control group. By combining the results of the above experiments, it is believed that H101 as an immunostimulant can effectively improve the tumor-inhibitive effect on the immunocompetent murine tumor model. Its efficacy is achieved not only by the direct oncolytic effect of the oncolytic virus, but further by promoting all the seven steps of anti-tumor immunity and effectively stimulating the anti-tumor immunity.

What is claimed is:

1. A method for treating a tumor and/or cancer, said method comprising the steps of:
    administering to a tumor and/or cancer patient an immunostimulating effective amount of a selectively replicating oncolytic virus as an immunostimulant in the treatment of the tumor and/or cancer,
    wherein the oncolytic virus does not carry an exogenous immunoregulatory gene, and wherein the immune function of the patient is sufficient to cause an anti-tumor cellular immune response, and the total number of leukocytes in whole blood of the patient is $\geq 4.0\times10^9$/L;
    wherein, 7-10 days after completion of the first course of consecutive administration, the immunostimulant is administered again to carry out an immune-boosting course, wherein the immune-boosting course is performed via intratumoral injection at a dose of $0.5\times10^{12}$ to $1.5\times10^{12}$ vp/day of the oncolytic virus, once daily, consecutively for 1 to 2 days, and
    wherein, the oncolytic virus is H101,
    wherein said method does not include any steps of either of chemotherapy and/or radiotherapy.

2. The method according to claim 1, wherein, in addition to directly killing tumor and/or cancer cells, the oncolytic virus also effectively induces activation and amplification of dendritic cells and T cells, induces up-regulation of the expression of chemokines at tumor and/or cancer cell sites, promotes the infiltration of dendritic cells and lymphocytes at tumor and/or cancer cell sites, and induces up-regulation of the expression of MHC-I and/or MHC-II molecules on tumor and/or cancer cells, thereby comprehensively stimulating the anti-tumor immune response of the patient.

3. The method according to claim 1, wherein the first course of consecutive administration of the immunostimulant is administered via intratumoral injection at a dose of $0.5\times10^{12}$ to $1.5\times10^{12}$ vp/day of the oncolytic virus, once daily, consecutively for 4 to 5 days.

4. The method according to claim 1, wherein the immunostimulant is administered in combination with one or more other tumor immunological agents.

5. The method according to claim 1, wherein the immune-boosting course is further repeated 2 to 3 times, at an interval of 7-10 days from the end of one immune-boosting course to the beginning of the next immune-boosting course.

* * * * *